United States Patent [19]

Kleeper et al.

[11] Patent Number: 4,534,220
[45] Date of Patent: Aug. 13, 1985

[54] APPARATUS FOR MEASURING THE CHARACTERISTICS OF AN ULTRASONIC WAVE MEDIUM

[76] Inventors: John R. Kleeper, 3238 Twenty Third Ave. W., Seattle, Wash. 98199; John M. Reid, 722 Upper Gulph Rd., Strafford, Pa. 19087; Hirohide Miwa, 6-7-10, Miyazaki, Miyamae-ku, Kawasaki-shi, Kanagawa 213, Japan; Takaki Shimura, 29-44, Tsurukawa 4-chome, Machida-shi, Tokyo 194-01, Japan; Keiichi Murakami, 17-305-2-8-6, Teraodai, Tama-ku, Kawasaki-shi, Kanagawa 214, Japan

[21] Appl. No.: 574,690

[22] Filed: Jan. 27, 1984

[51] Int. Cl.$^3$ ............................................. G01N 29/00
[52] U.S. Cl. ......................................... 73/599; 73/602
[58] Field of Search .......................... 73/599, 602, 620; 128/660; 364/821, 828, 731

[56] References Cited

U.S. PATENT DOCUMENTS

| | | | |
|---|---|---|---|
| 4,202,215 | 5/1980 | Heyer | 73/599 |
| 4,414,850 | 11/1983 | Miwa et al. | 73/602 |

*Primary Examiner*—Stephen A. Kreitman
*Attorney, Agent, or Firm*—Staas & Halsey

[57] ABSTRACT

The present invention relates to an apparatus which determines the distribution of the attenuation slope coefficient on a real time basis using the center frequency shift. The phase difference between a received signal and a reference signal is determined using EXCLUSIVE OR gates or an inverse trigonometric relation stored in a ROM. The phase difference is input to a differentiator which outputs the center frequency shift of the received signal on a real time basis. The center frequency shift is input to another differentiator which outputs the attenuation slope coefficient. Thus, the attenuation slope coefficient is determined using simple hardware and without calculating the power spectrum and the first moment.

17 Claims, 15 Drawing Figures

APPARATUS FOR MEASURING THE CHARACTERISTICS OF AN ULTRASONIC WAVE MEDIUM

BACKGROUND OF THE INVENTION

1. Field of the Invention

This invention relates to an apparatus for measuring the distribution of the ultrasonic wave attenuation constant of a medium, particularly to an apparatus utilizing the center frequency shift method for measuring ultrasonic wave attenuation constant distribution on a real time basis using simple hardware and without obtaining a reflected wave spectrum.

2. Description of the Prior Art

Figure 1:
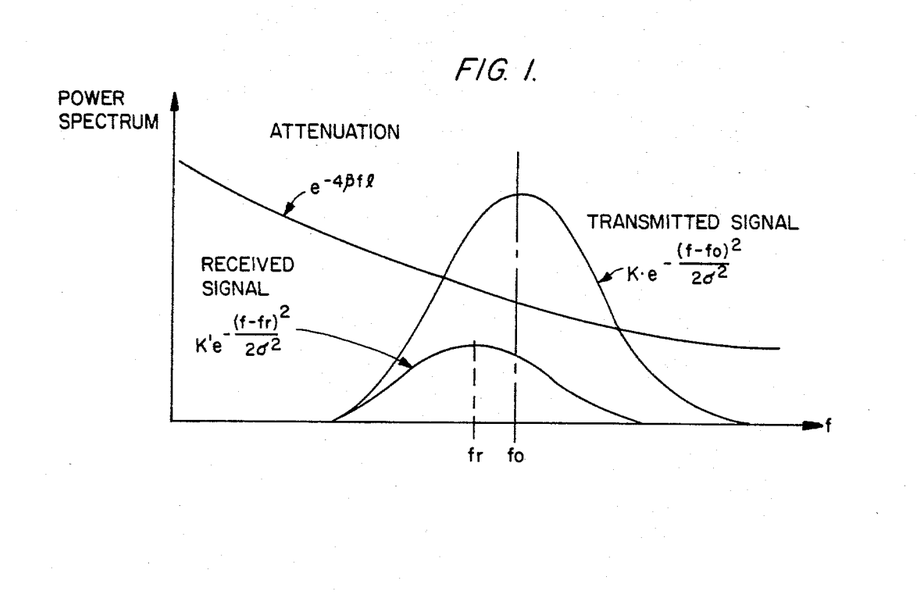
FIG. 1 is a graph of the power spectrum of transmitted and received signals.

The center frequency shift method is a known method for obtaining the attenuation constant in an ultrasonic wave medium. In this method, as illustrated in FIG. 1, the power spectrum A(f) of a transmitted ultrasonic wave has a Gaussian distribution expressed as $$A(f) = K e^{-[(f-f_o)^2/2\,\sigma^2]} \quad (1)$$

In equation (1), K is a constant, the variance $\sigma$ is a constant proportional to the bandwidth and dependent on the shape of the spectrum of the transmitted ultrasonic wave and $f_o$ is the center frequency. The power spectrum of the received signal A'(f) also has a Gaussian distribution which is expressed as follows where $f_r$ is the center frequency of the received signal:

$$A'(f) = K' e^{-[(f-f_r)^2/2\,\sigma^2]} \quad (2)$$

If it is assumed that the attenuation within the medium has the form:

$$e^{-4 \int_0^z \beta(z)dz} \quad (2a)$$

where z is the distance between the transmitting/receiving transducer and the reflecting surface, f is the frequency, $\beta$ is the attenuation slope coefficient and "4" allows for traversing the distance z twice and conversion of pressure into power, then K' and $f_r$ are defined by the following equations:

$$K' = K e^{\dfrac{\left[f_o - 4\sigma^2 \int_0^z \beta(z)dz\right]^2 - f_o^2}{2\sigma^2}} \quad (3)$$

$$f_r = f_o - 4\sigma^2 \int_0^z \beta(z)dz \quad (4)$$

Therefore, the attenuation slope coefficient $\beta$ can be obtained in the form indicated below by detecting the center frequency $f_r$ of the received signal.

$$\beta(z) = [1/(4\sigma^2)](f_o - f_r)\,d/dz \quad (5)$$

However, the received signal waveform is distorted and its spectrum deviates from a Gaussian distribution, and therefore the center frequency cannot be obtained easily. To overcome this problem, the following method has been used by the prior art to obtain the center frequency $f_r$. The power spectrum P(f) is first obtained by a Fourier transformation of the time domain waveform of the received signal for a certain time window T, and then the average frequency $\bar{f}$ is obtained according to equation (6) as the first moment of the power spectrum.

$$\bar{f} = \int_0^\infty f P(f) df \quad (6)$$

The average frequency $\bar{f}$ is then used as the center frequency $f_r$ in equation (5) and a value for the attenuation slope coefficient $\beta$ is obtained using equation (5).

A drawback of this method is the relatively large amount of time required for calculating the power spectrum and the first moment and therefore it has been difficult to obtain the distribution of $\beta$ on a real time basis.

SUMMARY OF THE INVENTION

An object of the present invention is to provide an apparatus which obtains the distribution of the attenuation slope coefficient on a real time basis by estimating the center frequency of a received signal from a profile of the phase difference between the received signal and a reference signal and by estimating a shift of the center frequency of the received signal on a real time basis using simple hardware and without calculating the power spectrum and the first moment.

The above object can be attained by providing a circuit which determines the phase difference between a received signal and a reference signal and passes the phase difference through a differentiating circuit to find the amount of frequency shift between the frequencies of the received signal and the reference signal. The signal representing the frequency shift amount passes through another differentiating circuit and is multiplied by a constant to find the attenuation slope coefficient. Several embodiments of the present invention utilize a quadrature/detector circuit and a signal conversion circuit to find the phase difference. The quadrature/detector circuit multiplies the received signal by the reference signal and by the reference signal shifted by 90° to generate two components defining the phase difference. These components and a trigonometric table stored in a ROM are used to find the phase difference in the signal conversion circuit. Another embodiment of the present invention generates the phase difference by passing the input signal simultaneously through two EXCLUSIVE OR circuits, the other input of one of the EXCLUSIVE OR circuits being the reference signal and the other EXCLUSIVE OR circuit receiving a signal corresponding to the reference signal shifted by 90°. From the output of these two EXCLUSIVE OR circuits, the phase difference can be determined. As a result, an apparatus according to the present invention obtains the attenuation slope coefficient without using the power spectrum and is therefore less expensive and operates in real time.

The above object, together with other objects and advantages which will be subsequently apparent, reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENTS

An apparatus according to the present invention determines the attenuation slope coefficient $\beta$ in real time instead of obtaining the power spectrum and the first moment. The phase of a received signal is compared with a reference signal, and if the phase difference is constant, the received signal has the same frequency as the reference signal. If the phase of the received signal increases over time compared to the reference signal, the received signal has a higher frequency, whereas if it decreases, the received signal has a lower frequency than the reference signal. Using this basic relationship between phase and frequency, the frequency difference $f_r - f_o$ between the received frequency $f_r$ and the reference frequency $f_o$ is obtained by differentiating the phase difference with respect to time and the attenuation slope coefficient $\beta$ is then obtained from equation (5).

The reference signal x(t) and received signal y(t) can be represented by the following equations in which $f_o$, $\theta_o$, $f_r$ and $\theta_r$ are constant if one uses the average frequency $\bar{f}$ for $f_r$ when the received signal includes more than one frequency:

$$x(t) = \sin(2\pi f_o t + \theta_o) \quad (7)$$

$$y(t) = \sin(2\pi f_r t + \theta_r) \quad (8)$$

The phase $\phi_o(t)$ of the received signal can then be represented as:

$$\phi_o(t) = 2\pi(f_r - f_o)t + (\theta_r - \theta_o) \quad (9)$$

and differentiating the above formula with respect to time leads to:

$$d\phi_o(t)/dt = 2\pi(f_r - f_o) \quad (10)$$

From equations (5) and (10) it is easy to see that the attenuation slope coefficient $\beta$ can be found using $d\phi_o/dt$.

Figure 2:
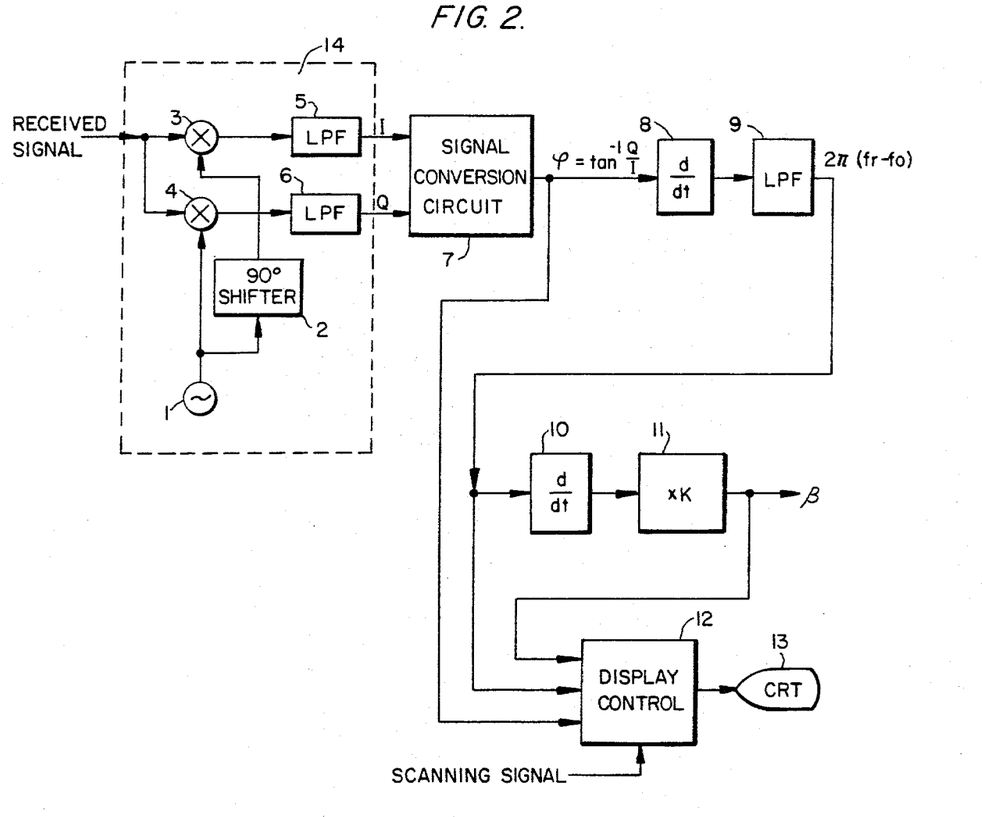
FIG. 2 is a block diagram of a first embodiment of the present invention.

FIG. 2 is a block diagram of a first embodiment of the present invention wherein a received signal is input to a quadrature/detector circuit 14 which includes a reference signal oscillator 1 with an oscillation frequency of $f_o$, a 90° phase shifter 2, multipliers 3 and 4, and low-pass filters 5 and 6. A reflected signal, having being received and amplified, is input as the received signal to the quadrature/detector 14 from which the components I and Q are obtained. The components I and Q are input to the signal conversion circuit 7 and $\phi = \tan^{-1}(Q/I)$ is output. The output of $\phi = \tan^{-1}(Q/I)$ obtained in the signal conversion circuit 7 is differentiated by a differentiating circuit 8 and is then smoothed by a low-pass filter 9.

Figure 3A:
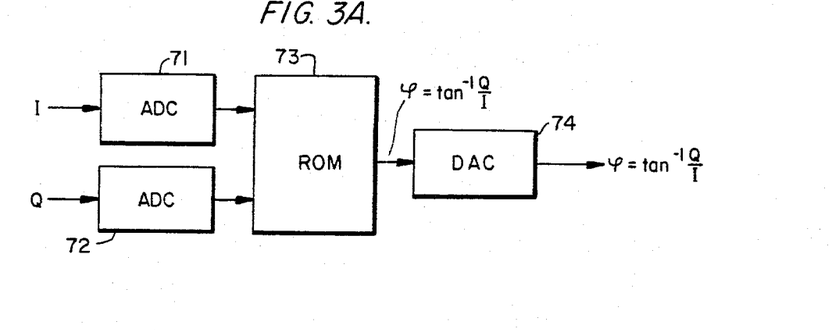
FIG. 3A is a block diagram of a first embodiment of the signal conversion circuit 7 in FIG. 2.

A first embodiment of the structure of the signal conversion circuit 7 is illustrated in FIG. 3A, in which components I and Q are converted from analog signals to digital signals in the analog/digital converters 71 and 72 and then input to the conversion table ROM 73 to determine $\tan^{-1}(Q/I)$. The value read out for $\tan^{-1}(Q/I)$ is converted to an analog signal in the digital/analog converter 74 and is then output as the phase $\phi$.

Figure 3B:
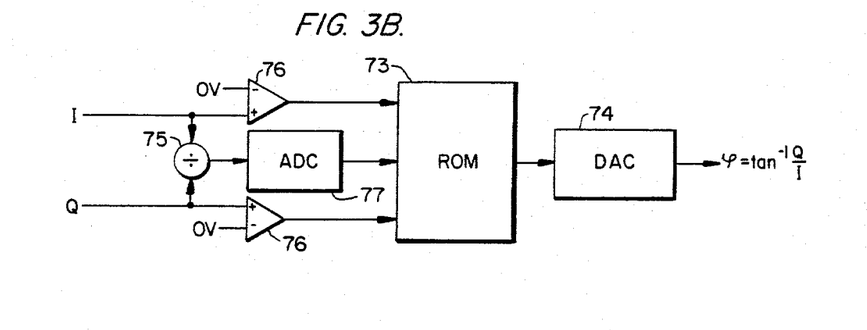
FIG. 3B is a block diagram of a second embodiment of the signal conversion circuit 7 in FIG. 2.

FIG. 3B is a second embodiment of the signal conversion circuit 7. As shown in FIG. 3B, it is also possible to obtain the value of the phase $\phi$ by dividing Q/I in an analog divider 75 and inputting it to the ROM 73 after converting Q/I to a digital signal in an analog/digital converter 77. The signs of I and Q, which specify the quadrant of the phase $\phi$ are determined by voltage comparators 76 and 78 and are input to the the ROM 73 along with the digital Q/I signal. This method offers advantages in that only one A/D converter is required and the table in the ROM 73 may be smaller without losing accuracy.

Figure 7A:
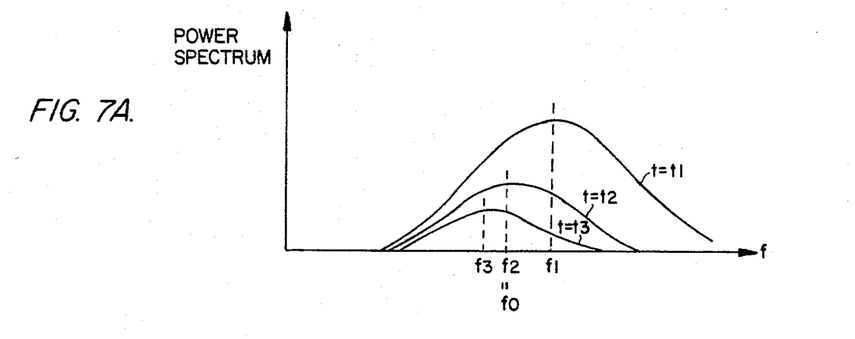
FIG. 7A is a graph of the power spectrum of the received signal.
Figures 7B, 7C:
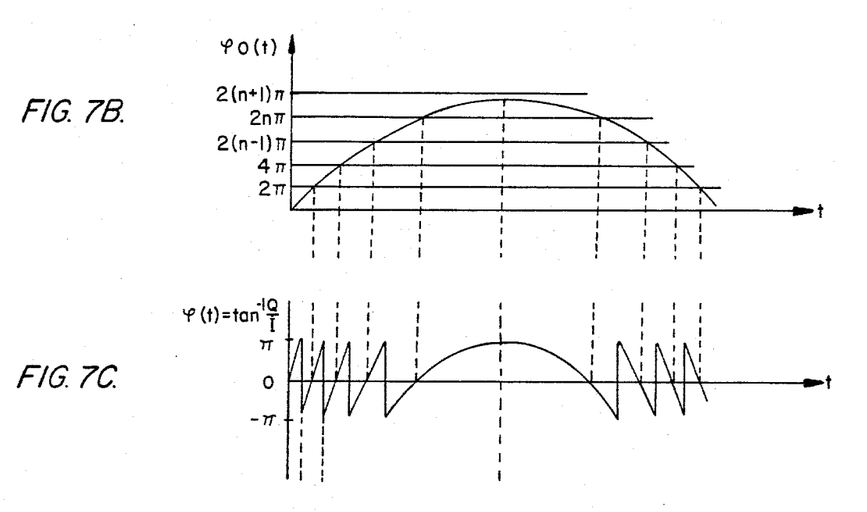
FIG. 7B and 7C are graphs of phase $\phi$ versus time.
Figure 7D:
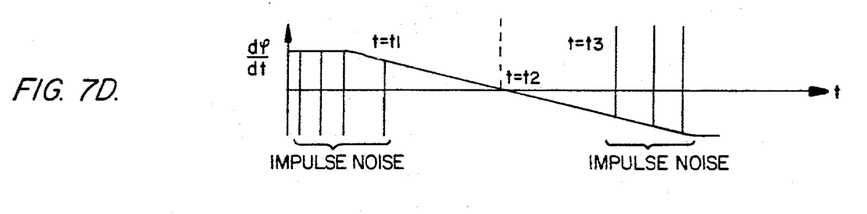
FIG. 7D is a graph of $d\phi/dt$ versus time.

FIGS. 7A-7D are graphs illustrating the process of obtaining respective signals until the center frequency shift $\Delta f = f_r - f_o$ is obtained. FIG. 7A is a graph of the power spectrum of the received signal. As time passes, $t = t_1, t_2, t_3, \ldots$, the ultrasonic wave is reflected from deeper areas, high frequency components are attenuated and the center frequency shifts to lower frequencies $f_2$ and $f_3$. FIGS. 7B-7D are profiles of the phase $\phi_o(t)$ and $d\phi(t)/dt$ which are obtained from $\phi(t) = \tan^{-1}(Q/I)$ when the reference frequency $f_o$ of the reference signal oscillator 1 is used as $f_2$. As can be easily estimated from equation (9) and as is illustrated in FIG. 7B, $\phi_o(t)$ increases continuously while the center frequency $f_r$ of the received spectrum is higher than $f_o$ (in the period where $t < t_2$), does not change when the center frequency $f_r$ is equal to the reference frequency $f_o$ (when $t = t_2$) and continuously decreases when the center frequency $f_r$ is lower than the reference frequency $f_o$ (in the period where $t > t_2$). The table in the ROM 73 gives values of $\phi(t) = \tan^{-1}(Q/I)$ within the range of $-\pi \leq \phi(t) \leq \pi$, so the values of $\phi(t)$ output by the signal conversion circuit 7 are as depicted in FIG. 7C. Therefore, $d\phi(t)/dt$, as depicted in FIG. 7D, includes impulse noise during the periods that $\phi(t)$ changes in value from $\pi$ to $-\pi$ (a change known as wrap around). The low-pass filter 9 in FIG. 2 is provided to eliminate such noise.

Figure 9:
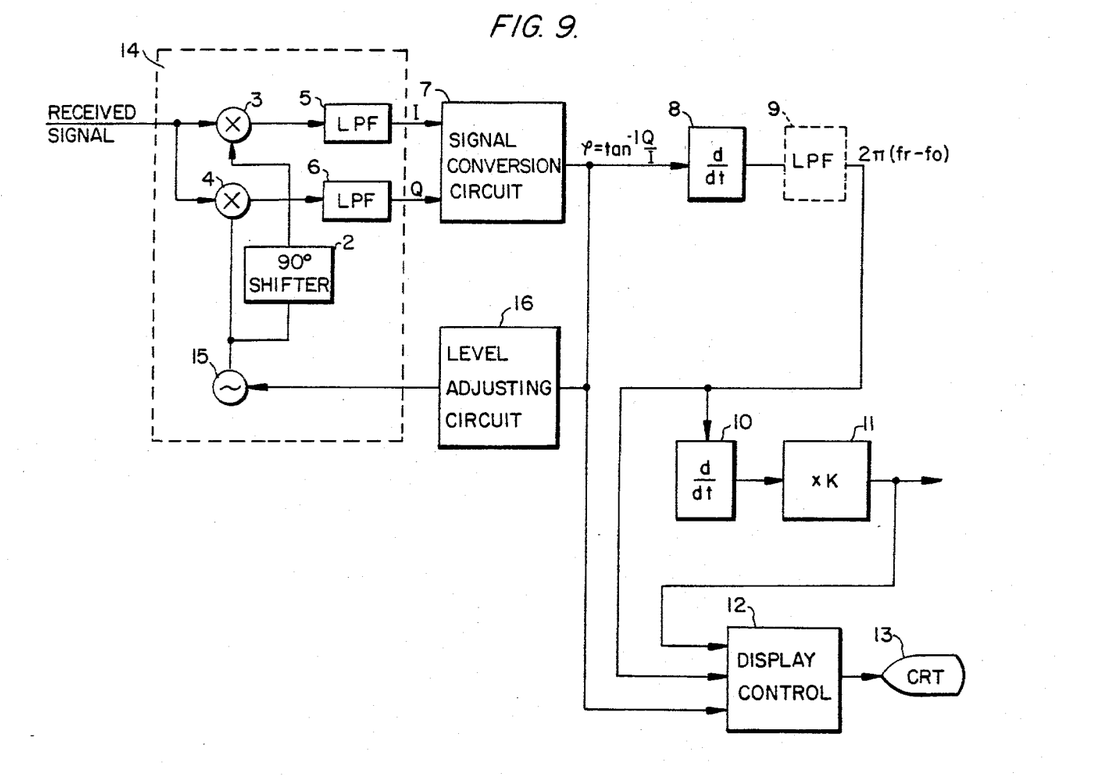
FIG. 9 is a block diagram of a second embodiment of the present invention.

When the difference $\Delta f$ between the reference frequency $f_o$ and the received frequency $f_r$ is large, $\phi_o(t)$ indicates a $2\pi$ change of phase within a very short period of time and, as a result, the impulse noise in the $d\phi(t)/dt$ signal increases considerably and can no longer be easily removed. A feedback loop that changes the reference frequency $f_o$ to be almost equal to the received frequency $f_r$ solves this problem so that $\phi(t)$ changes gradually. An embodiment of the present invention using such a feedback loop is illustrated in FIG. 9. In FIG. 9, the elements which are the same as those in FIG. 2 are given the same reference numerals and no further explanation of these elements is necessary. The only difference between the FIG. 9 circuit and the circuit of FIG. 2 is that the reference signal oscillator 1 is replaced by a variable frequency oscillator 15 for producing a reference frequency $f_o$ controlled by the signal from a level adjusting circuit 16 which leveladjusts the output ($\phi = \tan^{-1}(Q/I)$) of the signal conversion circuit 7. The reference frequency $f_o$ is controlled through the feedback loop so that the reference frequency $f_o$ is raised when $\phi(t)$ is increasing, and lowered when $\phi(t)$ is decreasing. Therefore, even if the center frequency (or average frequency) $f_r$ of the received signal drops, the reference frequency $f_o$ from the oscillator 15 also drops and $f_r - f_o$ is kept almost constant, so that wrap around will rarely occur because excessive changes in $\phi(t)$ are prevented. If wrap around is completely removed, the low-pass filter 9 is not needed.

Alternatively, other hardware or software could be used to generate values for $\phi(t)$ similar to those depicted in FIG. 7B. An example of a method for removing wrap around using software is given in J.M. Tribolet, "A New Phase Unwrapping Algorithm", IEEE TRANSACTIONS ON ACOUSTICS, SPEECH AND SIGNAL PROCESSING, VOL. ASSP-25, NO. 2, APRIL 1977, pp. 170–177. A block diagram of an alternate embodiment of the present invention utilizing software would look the same as FIG. 9, with the level adjusting circuit 16 comprising a microprocessor programmed to adjust the level of the variable oscillator 15.

As explained above, the output of the low-pass filter 9 of FIG. 2 $[d\phi(t)/dt]_{LPF}$ is proportional to the center frequency shift $\Delta f$. The attenuation slope coefficient $\beta$ in equation (5) can be obtained from the output $[d\phi(t)/dt]_{LPF}$ by dividing $[d\phi(t)/dt]_{LPF}$ by $-8\pi\sigma^2$ and differentiating it with respect to the distance z. But since $z = Ct$ where C is the velocity of sound which is assumed constant for applications of this invention and t is the time since sending the ultrasonic wave, differentiation with respect to z can be replaced by differentiation with respect to time t in the differentiating circuit 10 of FIG. 2. The attenuation slope coefficient $\beta(z)$ can be obtained by multiplying by a constant $K = -C/(8\pi\sigma^2)$ in the amplifier 11 after differentiation.

In the above explanation, the spectrum of the received signal is assumed to have a Gaussian distribution, as does the spectrum of the transmitted signal. Even if the received signal does not have a Gaussian distribution, since the average frequency shift is obtained by differentiating $\tan^{-1}(Q/I)$ with respect to time t, an approximate value of the attenuation slope coefficient $\beta$ will be obtained through the operations explained above. Also, $\tan^{-1}(Q/I)$ was obtained above as an analog signal and the differentiation and low-pass filtering were carried out on analog signals, but it is of course possible to use the output of the ROM 73 as a digital signal and then perform succeeding steps digitally.

Figure 8:
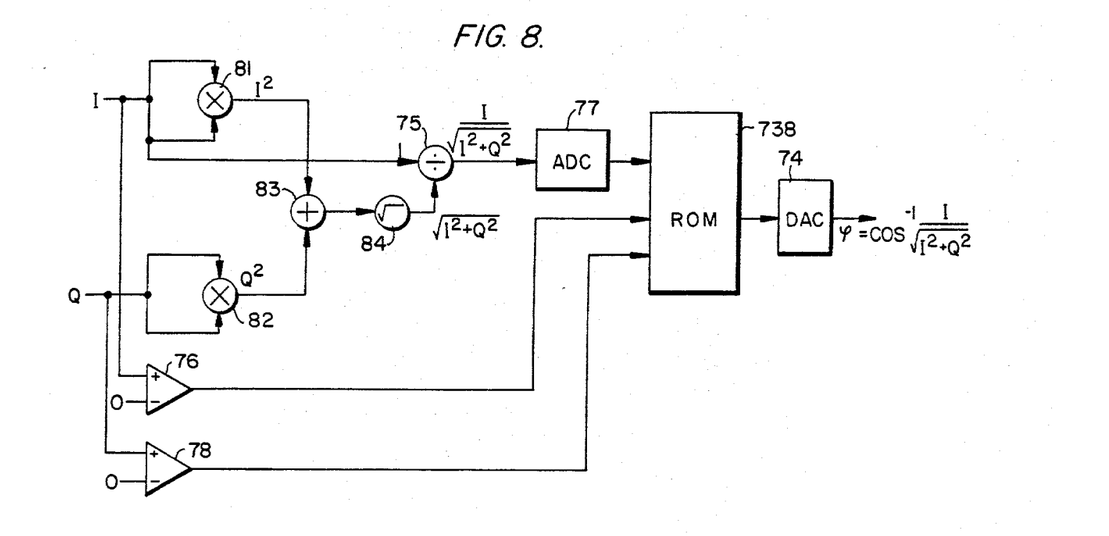
FIG. 8 is a block diagram of a third embodiment of the signal conversion circuit 7 in FIG. 2.

In another embodiment of the present invention, the phase $\phi$ is obtained using $\cos^{-1}$ or $\sin^{-1}$ in place of $\tan^{-1}$. A circuit which can be used as the signal conversion circuit 7 in FIG. 2 for finding $\phi = \cos^{-1}(I/\sqrt{I^2+Q^2})$ is illustrated in FIG. 8. The operation and purpose of the comparators 76 and 78, the divider 75, A/D converter 77, and D/A converter 74 in FIG. 8 are similar to the elements in FIG. 3B having the same reference numerals. The comparators 76 and 78 in FIG. 8 aid in distinguishing $0 \leq \phi \leq \pi$ from $\pi \leq \phi \leq 2\phi$. The difference between ROM 738 and ROM 73 is in the contents of the table. In FIG. 8, multipliers 81 and 82 form the square of components I and Q, respectively. An adder 83 sums the squares and a square root generating circuit 84 generates the divisor ($\sqrt{I^2+Q^2}$) for the divider 75. The square root generating circuit 84 as well as the multipliers 3, 4, 81 and 82 and divider 75 can all be implemented using an MC1595L multiplier manufactured by Motorola, and, as needed, an operational amplifier.

Figure 4:
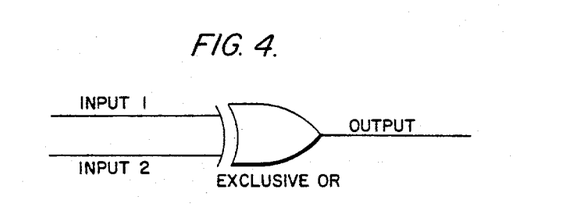
FIG. 4 is a symbolic diagram of an EXCLUSIVE OR gate.
Figure 5:
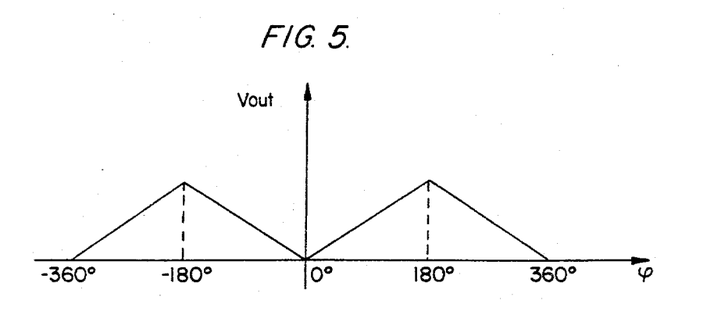
FIG. 5 is a graph of the relationship between phase $\phi$ and the mean voltage Vout output by an EXCLUSIVE OR gate.

In yet another embodiment of the present invention calculations such as $\tan^{-1}$ and $\cos^{-1}$ are omitted by employing a phase comparator which generates an output proportional to a phase difference. For example, as is well known, when a pair of square waves INPUT 1 and INPUT 2 are input to an EXCLUSIVE OR circuit as illustrated in FIG. 4, the mean value Vout of the output OUTPUT is proportional to the phase difference $\phi$ between the two square waves INPUT 1 and INPUT 2. The relation between $\phi$ and Vout becomes linear as shown in FIG. 5 and a value of $\phi = K'$Vout (where K' is a proportional constant) can be directly obtained without executing calculations of $\tan^{-1}$ and $\cos^{-1}$. However, as can be seen in FIG. 5, the same value of Vout is obtained for $\phi = +\theta$ and $\phi = -\theta$ and these values of $\phi$ cannot be distinguished when only two signals are used.

Figure 6A:
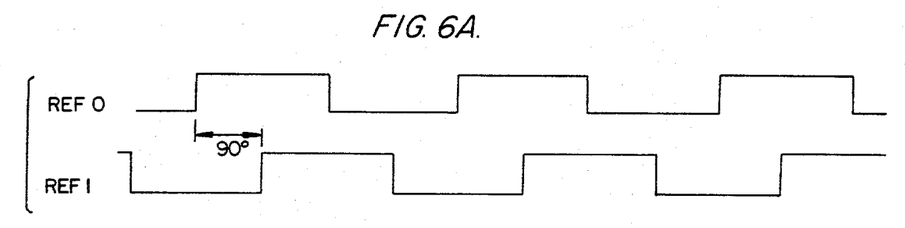
FIG. 6A is a graph of reference signals REF0 and REF1.
Figure 6B:
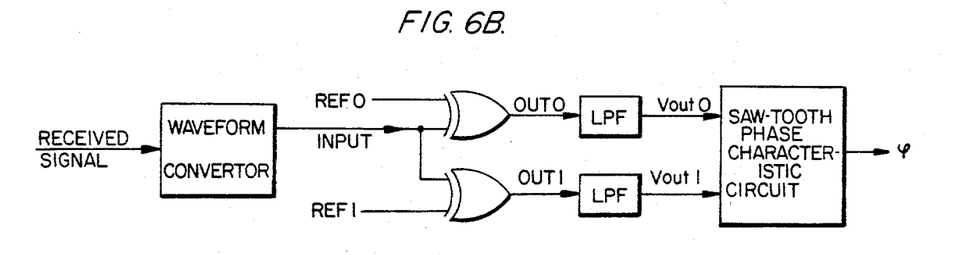
FIG. 6B is a symbolic diagram of the EXCLUSIVE ORing of an input signal INPUT with reference signals REF0 and REF1.
Figure 6C:
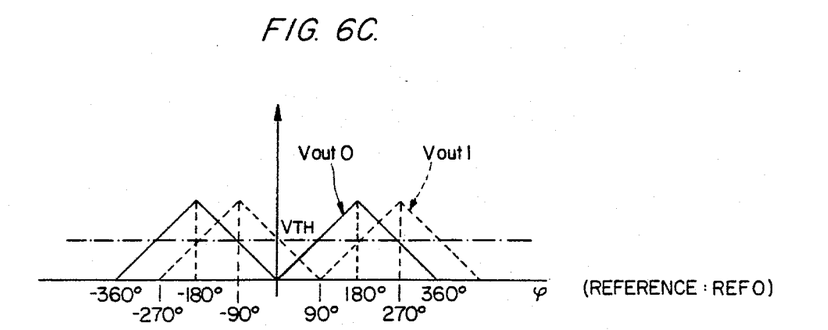
FIG. 6C is a graph of the relationship of the phase $\phi$ of the input signal to Vout0 and Vout1.

In this embodiment of the present invention, square waves REF0 and REF1 having a phase difference of 90° (as illustrated in FIG. 6A) are used as reference signals. The received signal is converted into a square wave INPUT by a waveform converter 60 which may comprise an amplifier and a level slicer (not shown). The converted receive signal is input to EXCLUSIVE ORs (61 and 62) along with each of the reference signals (REF0 and REF1, respectively) as illustrated in FIG. 6B. Low pass filters 63 and 64 are then used to generate mean values Vout0 and Vout1 from the outputs OUT0 and OUT1, respectively. The relationship between the phase $\phi$ of the converted received signal INPUT and Vout0 and Vout1 is the saw-tooth phase characteristic illustrated in FIG. 6C and therefore:

Vout1 $\leq$ V$_{TH}$ $\rightarrow$ $\phi \geq 0$

Vout1 $>$ V$_{TH}$ $\rightarrow$ $\phi < 0$ for $-180° \leq \leq 180°$. From the above relationship, the sign (positive or negative) of the phase $\phi$ can be determined. It is obvious that the absolute value of the phase $|\phi|$ can be easily obtained from $|\phi| = K'$Vout0 and therefore the phase $\phi$ itself can be obtained easily in the saw-tooth phase characteristic circuit 65 without the complicated calculations required for finding the $\tan^{-1}$ and $\cos^{-1}$ functions.

In another alternate embodiment of the present invention, the phase difference $\phi$ between the received signal and the reference signal is obtained by sampling the received signal at a frequency of several MHz after direct A/D conversion and by finding the phase difference $\phi$ by digital processing of the sampled data using software or hardware. An example of a structure using digital processing is a combination of a high speed waveform sampling system and a computer.

After determining the values of $\phi$, $\Delta f$, $f_r$ and $\beta$ as described above, an embodiment of the present invention includes an apparatus for supplying these values to a CRT display 13 as can be seen in FIGS. 2 and 9. A tomographic image of an object to be measured can be displayed by supplying signals representing $\phi$, $\Delta f$, $f_r$ and $\beta$ to the display controller 12 as brightness signals. These signals are then supplied to the CRT 13 together with the pertinent synchronous signal, blanking signal and deflection signal related to the ultrasonic scanning of the object to be measured. A color display can, of course, be generated by assigning colors to $\phi$, $\Delta f$, and $\beta$.

According to this invention, as explained above, the frequency shift $\Delta f$ of a reflected ultrasonic wave passing through a measuring medium and the attenuation slope coefficient $\beta$ of the ultrasonic wave in the measuring medium can be obtained on a real time basis using a simple circuit in place of a relatively expensive and low speed device which obtains a power spectrum of the received signal.

The many features and advantages of the invention are apparent from the detailed specification and thus it is intended by the appended claims to cover all such features and advantages of the system which fall within the true spirit and scope of the invention. Further, since numerous modifications and changes will readily occur to those skilled in the art, it is not desired to limit the invention to the exact construction and operation illustrated and described, accordingly, all suitable modifications and equivalents may be resorted to, falling within the scope of the invention.

What is claimed is:

1. An apparatus for measuring ultrasonic wave attenuation and phase by sending an ultrasonic wave pulse toward an object to be measured, and receiving, as a received signal, waves reflected from different depths within the object to be measured, comprising:
   means for supplying a reference signal;
   means, operatively connected to said reference signal supplying means and operatively connected to receive the received signal, for determining a phase difference between the received signal and the reference signal;
   first differentiating means, operatively connected to said phase difference determining means, for differentiating the phase difference with respect to time to generate a frequency shift amount signal; and
   second differentiating means, operatively connected to said first differentiating means, for differentiating the frequency shift amount signal with respect to time to generate an attenuation slope coefficient.

2. An apparatus as recited in claim 1, wherein said phase difference determining means comprises:
   a quadrature/detector circuit, operatively connected to said reference signal supplying means and operatively connected to receive the received signal, for separating the received signal into an in-phase component and a quadrature component; and
   a signal conversion circuit, operatively connected to said quadrature/detector circuit and said first differentiating means, for determining the phase difference based on an inverse trigonometric function using the in-phase component and the quadrature component of the received signal.

3. An apparatus as recited in claim 2, wherein said quadrature/detector circuit comprises:
   a 90° phase shifter circuit, operatively connected to said reference signal supplying means, for shifting the reference signal by 90°;
   a first multiplier circuit operatively connected to said 90° phase shifter circuit and operatively connected to receive the received signal;
   a second multiplier circuit operatively connected to said reference signal supplying means and operatively connected to receive the received signal;
   a first low-pass filter, operatively connected to said first multiplier circuit and said signal conversion circuit, for outputting the in-phase component of the received signal; and
   a second low-pass filter, operatively connected to said second multiplier circuit and said signal conversion circuit, for outputting the quadrature component of the received signal.

4. An apparatus as recited in claim 2, wherein said signal conversion circuit comprises:
   a first analog/digital converter, operatively connected to said quadrature/detector circuit, for converting the in-phase component of the received signal into a digital in-phase component;
   a second analog/digital converter, operatively connected to said quadrature/detector circuit, for converting the quadrature component of the received signal into a digital quadrature component;
   a read only memory, operatively connected to said first and second analog/digital converters, for determining a digital phase difference as the arctangent of a quantity defined by the digital quadrature component divided by the digital in-phase component; and
   a digital/analog converter, operatively connected to said read only memory and said first differentiating means, for outputting the phase difference by converting the digital phase difference into an analog signal.

5. An apparatus as recited in claim 2, wherein said signal conversion circuit comprises:
   a divider circuit, operatively connected to said quadrature/detector circuit, for dividing the quadrature component of the received signal by the in-phase component of the received signal and generating a divided output;
   a first comparator, operatively connected to said quadrature/detector circuit, for outputting the sign of the in-phase component of the received signal;
   a second comparator, operatively connected to said quadrature/detector circuit, for outputting the sign of the quadrature component of the received signal;
   an analog/digital converter, operatively connected to said divider circuit, for converting the divided output into a digital divided output;
   a read only memory, operatively connected to said first and second comparators, and said analog/digital converter, for determining the arctangent of the digital divided output in a quadrant identified by the sign of the in-phase and quadrature components of the received signal; and a digital/analog converter, operatively connected to said read only memory and said first differentiating means, for outputting the phase difference by converting the arctangent of the digital divided output into an analog signal.

6. An apparatus as recited in claim 2, wherein said signal conversion circuit comprises:

a first multiplier circuit, operatively connected to said quadrature/detector circuit, for squaring the in-phase component of the received signal;

a second multiplier circuit, operatively connected to said quadrature/detector circuit, for squaring the quadrature component of the received signal;

a first comparator, operatively connected to ground and to said quadrature/detector circuit, for outputting the sign of the in-phase component of the received signal;

a second comparator, operatively connected to ground and to said quadrature/detector circuit, for outputting the sign of the quadrature component of the received signal;

an adder, operatively connected to said first and second multipliers, for summing the squares of the in-phase and quadrature components of the received signal;

a square root generating circuit, operatively connected to said adder, for generating the square root of the sum of the squares of the in-phase and quadrature components of the received signal;

a divider, operatively connected to said square root generating circuit and said quadrature/detector circuit, for generating a divided output corresponding to the in-phase component of the received signal divided by the square root of the sum of the squares of the in-phase and quadrature components of the received signal;

an analog/digital converter, operatively connected to said divider, for converting the divided output into a digital divided output;

a read only memory, operatively connected to said first and second comparators and said analog/digital converter, for determining the arccosine of the digital divided output; and a digital/analog converter, operatively connected to said read only memory and said first differentiating means, for outputting the phase difference by converting the arccosine of the digital divided output into an analog signal.

7. An apparatus as recited in claim 1, wherein the reference signal has a period and wherein said phase difference determining means comprises:

waveform converting means, operatively connected to receive the received signal, for converting the received signal into an input signal representing the sign of the received signal;

mean value generating means, operatively connected to said waveform converting means and said reference signal supplying means, for generating a mean value signal representing an amount of time that the input signal and reference signal are opposite in sign divided by the period of the reference signal; and saw-tooth phase means, operatively connected to said mean value means and said first differentiating means, for comparing the mean value signal with a saw-tooth phase characteristic to determine the phase difference.

8. An apparatus as recited in claim 7, wherein said reference signal supplying means supplies first and second square wave reference signals, the second square wave reference signal being 90° out of phase with the first square wave reference signal, and wherein said mean value generating means comprises:

a first EXCLUSIVE OR gate, operatively connected to said waveform converting means, and said reference signal supplying means, for EXCLUSIVE ORing the input signal and the first square wave reference signal;

a second EXCLUSIVE OR gate, operatively connected to said waveform converting means and said reference signal supplying means, for EXCLUSIVE ORing the input signal and the second square wave reference signal;

a first low pass filter operatively connected to said first EXCLUSIVE OR gate and said saw-tooth phase means; and a second low pass filter operatively connected to said second EXCLUSIVE OR gate and said saw-tooth phase means.

9. An apparatus as recited in claim 1, wherein said phase difference determining means comprises:

means, operatively connected to receive said received signal, for sampling the received signal at a rate higher than the frequency of the received signal;

means, operatively connected to said sampling means, for storing the samples of the received signal; and digital processing means, operatively connected to said storing means, said reference signal supplying means and said first differentiating means, for obtaining the phase difference using digital processing.

10. An apparatus as recited in claim 9, wherein said digital processing means comprises:

component means, operatively connected to said storing means and said reference signal supplying means, for separating the received signal into an in-phase component which is in phase with the reference signal and a quadrature component which is orthogonal to the in-phase component; and trigonometric relation means, operatively connected to said component means and said first differentiating means, for determining the phase difference from a trigonometric relation between the in-phase and quadrature components of the received signal.

11. An apparatus as recited in claim 10, wherein said trigonometric relation means comprises means, operatively connected to said component generating means and said first differentiating means, for calculating the arctangent of a quantity defined by the quadrature component divided by the in-phase component.

12. An apparatus as recited in claim 10, wherein said trigonometric relation means comprises means, operatively connected to said component generating means and said first differentiating means, for calculating the arccosine of a quantity defined by the in-phase component divided by the square root of the sum of the squares of the in-phase and quadrature components.

13. An apparatus as recited in claim 1, wherein the reference signal supplied by said reference signal supplying means has a variable frequency, and further comprising a level adjusting circuit, operatively connected to said phase difference determining means and said reference signal supplying means, for varying the frequency of the reference signal in accordance with the phase difference.

14. An apparatus as recited in claim 1, further comprising means, operatively connected to at least one among said phase difference determining means and said first and second differentiating means, for displaying at least one among the phase difference, frequency shift amount signal, and attenuation slope coefficient corresponding to the different depths from which the ultrasonic wave pulse was reflected.

15. A method for measuring ultrasonic wave attenuation, comprising the steps of:
(a) sending an ultrasonic wave pulse toward an object to be measured;
(b) receiving a received signal comprised of ultrasonic waves reflected from different depths;
(c) generating a reference signal;
(d) determining a phase difference between the received signal and the reference signal;
(e) differentiating the phase difference with respect to time to generate a frequency shift amount; and
(f) differentiating the frequency shift amount with respect to time to generate an attenuation slope coefficient.

16. A method as recited in claim 15, wherein step (d) comprises the substeps of:
(di) separating the received signal into an in-phase component and a quadrature component; and
(dii) calculating a value for an inverse trigonometric function using the in-phase and quadrature components of the received signal to determine the phase difference.

17. A method as recited in claim 15,
wherein the reference signal generated in step (c) includes first and second square wave reference signals which have a period which is the same for both the first and second square wave reference signals, the second square wave reference signal being 90° out of phase with the first square wave reference signal, and
wherein step (d) comprises the substeps of:
(di) converting the received signal into an input square wave signal;
(dii) calculating first and second mean values which are equal to the amount of time the first and second square wave reference signals, respectively, have the same sign as the input square wave signal divided by the period of the first and second square wave signals; and
(diii) comparing the first and second mean values with a saw-tooth phase characteristic to determine the phase difference.

* * * * *

UNITED STATES PATENT AND TRADEMARK OFFICE
CERTIFICATE OF CORRECTION

PATENT NO. : 4,534,220

DATED : August 13, 1985

INVENTOR(S) : Klepper et al.

It is certified that error appears in the above-identified patent and that said Letters Patent is hereby corrected as shown below:

```
Front Page, "Kleeper et al." should be --Klepper et al.--;
[76] Inventors, "John R. Kleeper" should be
     --John R. Klepper--.
Column 1, line 37, [formula 2a] after "4" insert --f--.
Column 6, line 12, "ZØ" should be --2 π--;
         line 38, "+O" should be --+θ--;
         line 61, "≤ ≤" should be --≦ Ø ≦--.
```

Signed and Sealed this

Eleventh Day of February 1986

[SEAL]

*Attest:*

DONALD J. QUIGG

*Attesting Officer*     *Commissioner of Patents and Trademarks*